United States Patent
Casonato (10) Patent No.: US 9,016,677 B2
(45) Date of Patent: Apr. 28, 2015

(54) LOADING CONTAINER FOR A WASHING MACHINE

(75) Inventor: Ottorino Casonato, Castelfranco Veneto (IT)

(73) Assignee: Steelco SpA, Riese Pio X (IT)

( * ) Notice: Subject to any disclaimer, the term of this patent is extended or adjusted under 35 U.S.C. 154(b) by 791 days.

(21) Appl. No.: 13/379,842

(22) PCT Filed: Jun. 23, 2010

(86) PCT No.: PCT/IB2010/001507
§ 371 (c)(1),
(2), (4) Date: Dec. 21, 2011

(87) PCT Pub. No.: WO2010/150075
PCT Pub. Date: Dec. 29, 2010

(65) Prior Publication Data
US 2012/0098181 A1     Apr. 26, 2012

(30) Foreign Application Priority Data

Jun. 24, 2009   (IT) .......................... UD2009A000120

(51) Int. Cl.
| B23Q 1/25 | (2006.01) |
| --- | --- |
| D06F 33/00 | (2006.01) |
| D06F 21/00 | (2006.01) |
| D06F 23/00 | (2006.01) |
| D06F 37/00 | (2006.01) |
| A61B 19/00 | (2006.01) |
| A47L 15/50 | (2006.01) |

(52) U.S. Cl.
CPC .............. *A61B 19/34* (2013.01); *A47L 15/506* (2013.01); *A47L 15/507* (2013.01); *A61B 2019/343* (2013.01)

(58) Field of Classification Search
USPC ....... 269/55; 68/139, 23 R, 12.05, 208, 17 A, 68/12.01
See application file for complete search history.

(56) References Cited

U.S. PATENT DOCUMENTS

| 2,521,159 | A | * | 9/1950 | Geldhof et al. .............. 68/12.05 |
| --- | --- | --- | --- | --- |
| 2,526,444 | A | * | 10/1950 | Woodson ...................... 68/12.01 |
| 2,533,722 | A | * | 12/1950 | De Remer ...................... 68/23.3 |
| 3,195,327 | A | * | 7/1965 | Cobb ............................ 68/12.01 |
| 3,290,908 | A | * | 12/1966 | McAllister et al. ........... 68/17 A |
| 3,290,909 | A | * | 12/1966 | Schwing et al. .............. 68/23 R |

(Continued)

FOREIGN PATENT DOCUMENTS

| DE | 3710349 A1 | 10/1988 |
| --- | --- | --- |
| EP | 1949868 A1 | 7/2008 |

OTHER PUBLICATIONS

Int'l Search Report issued Sep. 17, 2010 in Int'l Application No. PCT/IB2010/001507; Written Opinion.

*Primary Examiner* — Lee D Wilson
*Assistant Examiner* — Alvin Grant
(74) *Attorney, Agent, or Firm* — Panitch Schwarze Belisario & Nadel LLP (57) ABSTRACT

A loading container (10) for a washing machine (60) comprises a containing body (12) to support and position objects to be washed inside the washing machine (60) or washing devices (20, 22) containing the objects to be washed. The container (10) also comprises a base body (14), located below the containing body (12), and a rotation unit (45) to connect rotatably the base body (14) and the containing body (12) so as to allow a selective reciprocal angular positioning of the containing body (12) and the base body (14).

15 Claims, 4 Drawing Sheets

(56) References Cited

U.S. PATENT DOCUMENTS

| | | | |
|---|---|---|---|
| 3,301,023 A * | 1/1967 | Painter | 68/12.05 |
| 3,312,087 A * | 4/1967 | Toma | 68/12.05 |
| 3,333,444 A * | 8/1967 | Bochan | 68/208 |
| 4,763,678 A | 8/1988 | Ott | |
| 5,425,815 A * | 6/1995 | Parker et al. | 134/26 |
| 6,068,815 A * | 5/2000 | Oberleitner et al. | 422/28 |
| 2005/0112040 A1 | 5/2005 | Hasegawa et al. | |
| 2010/0050700 A1* | 3/2010 | Bongini | 68/139 |

* cited by examiner

STATE OF THE ART fig. 1 fig. 2 fig. 3 fig. 3a fig. 4

US 9,016,677 B2

LOADING CONTAINER FOR A WASHING MACHINE

CROSS-REFERENCE TO RELATED APPLICATION

This application is a Section 371 of International Application No. PCT/IB2010/001507, filed Jun. 23, 2010, which was published in the English language on Dec. 29, 2010, under International Publication No. WO 2010/150075 A1, and the disclosure of which is incorporated herein by reference.

FIELD OF THE INVENTION

The present invention concerns a loading container, also commonly called a basket or rack, to load, position and directly support objects which have to undergo a washing treatment inside a washing machine, or devices inside which said objects are treated by washing, and which, in their turn, can be inserted inside said washing machine. The objects to be treated can be, for example, medical instruments of the tubular type made of various materials, in particular metal, plastic and/or rubber, typically endoscopic instruments, such as colonoscopes, bronchoscopes and gastroscopes. In particular, the treatment, directly in the washing chamber of the washing machine or inside the washing device, is washing, chemical disinfecting, drying and draining of these instruments. However, it cannot be excluded that the container according to the present invention may also be used as a basket or rack in order to directly support objects to be washed inside dishwashers, of the domestic or industrial type, or other household washing machines.

BACKGROUND OF THE INVENTION

It is known to treat medical instruments of the endoscopic type, which get dirty during use, in a suitable washing chamber in a washing machine, by means of complete washing both of the external surfaces and of the inside surfaces and channels. There are flexible tubes inside the washing chamber to connect with the inside channels of the endoscopic instrument which, by means of a watertight connector, are put in connection with devices to deliver the washing liquid associated with the washing machine. The endoscopic instrument is treated externally, on the other hand, by immersion in a container, for example an auxiliary washing pipe, in the same washing chamber. The washing liquid, by means of a sleeve mounted on the auxiliary piping, is delivered inside, in order to reach all the external surface of the insertion pipe. Moreover, since the insertion pipe is usually very long, in order to be easily disposed in the basket and loaded in the washing chamber, it has to be wound in a spiral and keep the spiral shape in the washing chamber. To do this, said washing pipe is shaped as a spiral.

A washing pipe or device of the type in question, with relative container or support basket, is described in the European patent application EP-A-1.949.868 (EP'868). In particular, in the attached FIG. 1 (state of the art) the container of EP'868 is shown, indicated by the reference number 100, associated with a pair of spiral washing pipes 120, 122 inside each of which a relative endoscope to be washed is inserted. It is common practice to provide that these containers support a pair of washing pipes, so as to increase productivity, positioned angularly offset by 180° with respect to each other. The container 100 of EP'868 is formed by an upper frame 112 and by a base frame 114. The base frame 114 provides sliding rollers 118, for insertion into the washing machine, for example in the direction indicated by the arrow G. The hydraulic connection sleeves 121, 123 of the spiral washing pipes 120, 122 are supported by means of rings 117 positioned by means of brackets 16.

Figure 1:
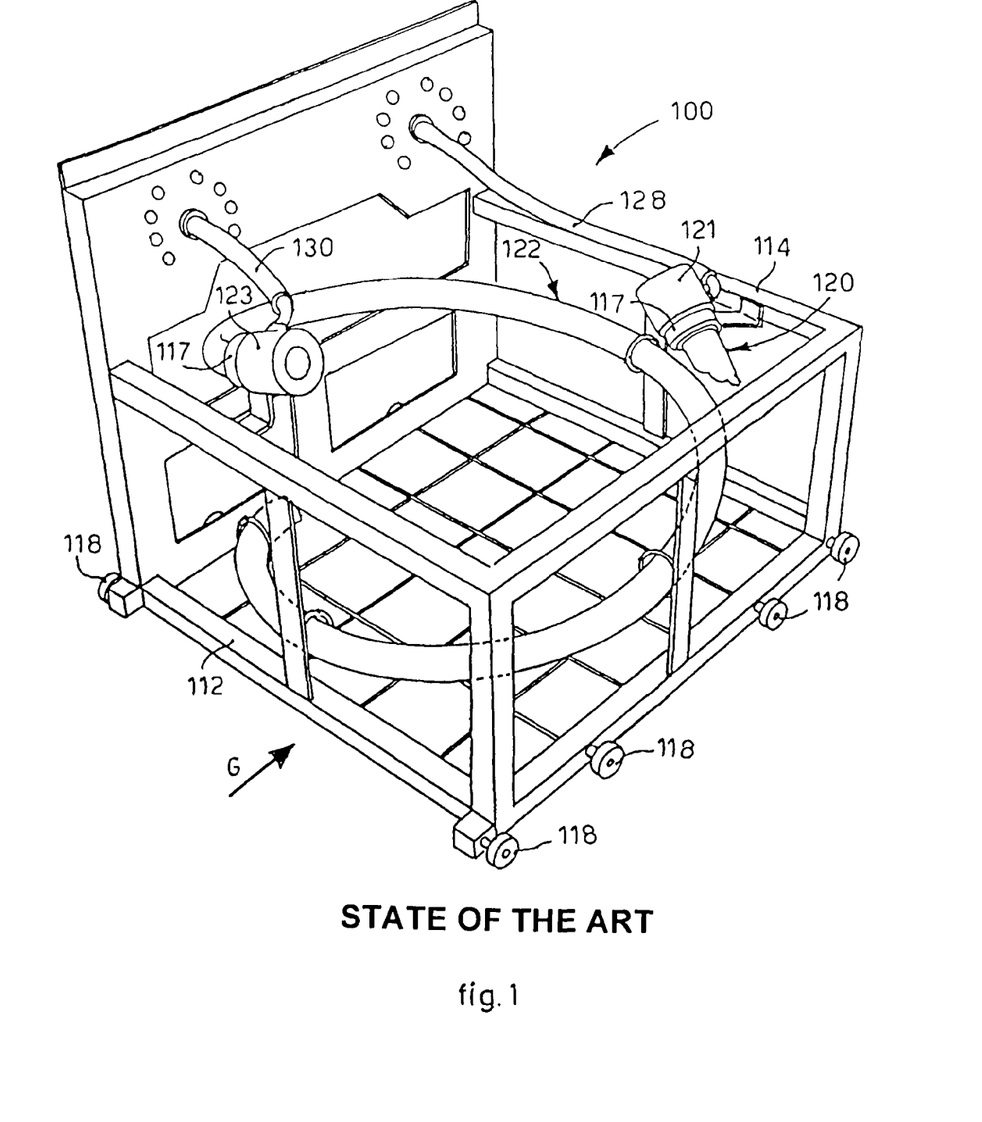
FIG. 1 is a perspective view of a state of the art container.

In this way, during the insertion of the container 100 into the washing machine, on the front side of the container facing toward the operator, the hydraulic connection sleeve 123 of one of the two spiral washing pipes is presented to the operator, while on the opposite side, therefore on the rear side and facing toward the inside of the washing machine, there is the hydraulic connection sleeve 121 of the other spiral washing pipe.

However, this disposition of the two sleeves 121, 123 does not promote easy operation by the operator, who, if he/she is not very tall, or if the washing machine is close to a wall and therefore with a reduced working space, has difficulty in reaching the rear sleeve 121 for the hydraulic connection.

A loading container for a washing machine is known from the document DE-A-3710349. A cleaning apparatus for oblong objects is also known from document U.S. Pat. No. 4,763,678.

Purpose of the present invention is to achieve a loading container to position and support objects to be washed, or washing devices inside which objects to be washed are disposed, which is ergonomic for the operator to use.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purpose, a loading container, also commonly called basket or rack, for a washing machine, comprises a containing body to support and position the objects to be washed inside the washing machine or washing devices containing the objects to be washed.

The container according to the present invention also comprises a base body, located below the containing body, and a rotation unit able to connect the base body and the containing body rotatably, so as to allow a selective reciprocal angular positioning of the containing body and the base body.

According to the present invention, the rotation unit comprises:

a supporting and sliding wall, attached to the base body, which comprises a rotation pin;

a support structure attached below the containing body, which has a rotation seating for said rotation pin, so as to pivot said containing body to said rotation pin in order to slide in rotation along said supporting and sliding wall.

The rotation of the containing body and the base body allows an operator to position the containing body above as desired, in order to have easy access to the various objects or washing devices contained and supported by the containing body. In this way, the container of the present invention has optimal ergonomics for the operator, who can easily access even objects or parts of washing devices which are at a distance.

In particular the operator can easily reach, in a first rotated angular position, a determinate object or device and subsequently, simply by rotating the containing body on itself in a second rotated angular position, he/she can easily have access also to another object or device that, for example, in the first rotated angular position is in a distant and difficult to reach position. Moreover the containing body can be rotated even in an angular position aligned with the base body below, in order to allow insertion in a washing chamber of the washing machine.

The sliding in rotation of the containing body on the support and sliding wall allows a good stability in rotation of the containing body above.

The present invention is advantageous both for single-door washing machines and for through washing machines with separate entrance and exit doors.

In particular, when spiral washing devices as in EP'868 are used, the invention allows an easy access to the sleeves for their hydraulic connection, above all when one is on one side of the container and the other is on the other side. This advantage of the present invention is appreciated at the exit of both a through washing machine and also a single-door washing machine, situations where it is necessary to disconnect the hydraulic connections and there would once again be a problem of accessibility for some distant objects or parts of washing devices.

In some forms of embodiment, the base body is advantageously of the transferable type. In particular, the base body is provided with first linear sliding means, for example rollers, for an easy movement of the container, in particular during the insertion into the washing machine. In this way, it is possible to combine a rotation movement of the containing body on itself with respect to the base body, which movement can be used in the loading and access steps of the objects and/or the washing devices, with a movement of the linear type of the container in its entirety, used for example in the moving and insertion steps.

According to a variant, the rotation unit is conformed so as to allow a relative rotation of the containing body and the base body around an axis of rotation passing substantially through the center of the containing body and the base body. The central rotation allows to have reduced bulk and increased constructive simplicity.

Another variant provides that the supporting and sliding wall is advantageously of an annular shape, attached to the base body.

A variant embodiment provides that the base body comprises a base frame, advantageously provided with said first sliding means. In order to make everything compact, said supporting and sliding wall is attached inside the base frame of the base body.

In some forms of embodiment said support structure attached below the containing body supports and positions second sliding means, for example wheels, advantageously able to cooperate with said supporting and sliding wall.

In some forms of embodiment, the rotation pin which cooperates with the rotation seating is provided centrally on the supporting wall below.

A constructional variant provides that the support structure is configured in a radial structure, comprising a plurality of radial plates with peripheral ends which bear said second sliding means. This solution reduces the weight and bulk of everything, as well as integrating in an optimal manner with the rotational needs of the container according to the invention.

In some forms of embodiment, the radial support structure is formed by six radial plates or spokes, angularly offset by 60°, having peripheral ends attached to the containing body.

In further forms of embodiment, said supporting and sliding wall comprises an annular track attached to said base body by means of connecting elements, which is provided with spokes and centrally supports and positions said rotation pin, facing upward.

According to a constructional solution which reduces the weight and also facilitates cleaning, the containing body comprises a lower frame, an upper frame and vertical connection uprights between said lower frame and upper frame. In this embodiment, the support structure is attached below the lower frame, thus cooperating by means of said sliding means directly with the annular supporting wall below.

Advantageously, the base frame of the base body and the lower and upper frames of the containing body are mating in size, so that, in the operating condition of alignment for insertion into the washing machine, these are aligned, substantially fitting together along the respective external edges.

In a variant solution, the present invention also comprises a clamping or stopping device, which can be selectively activated in order to allow the clamping of the relative rotation between the containing body and the base body: this is an advantageous condition for example during insertion into the washing chamber or for other movement maneuvers of the container.

According to one form of embodiment, the clamping device comprises stopping means, for example levers, rotatably associated with one or both sides of the base body, which are able to be rotated so as to selectively assume a clamping condition in which they determine an obstacle to the rotation of the containing body.

In some forms of embodiment of the present invention, said clamping device comprises an automatic return mechanism of said stopping means, from a second operating condition of non-interference with said containing body to the clamping condition of the containing body.

BRIEF DESCRIPTION OF THE DRAWINGS

These and other characteristics of the present invention will become apparent from the following description of a preferential form of embodiment, given as a non-restrictive example with reference to the attached drawings wherein.

DETAILED DESCRIPTION OF A PREFERENTIAL FORM OF EMBODIMENT

Figure 4:
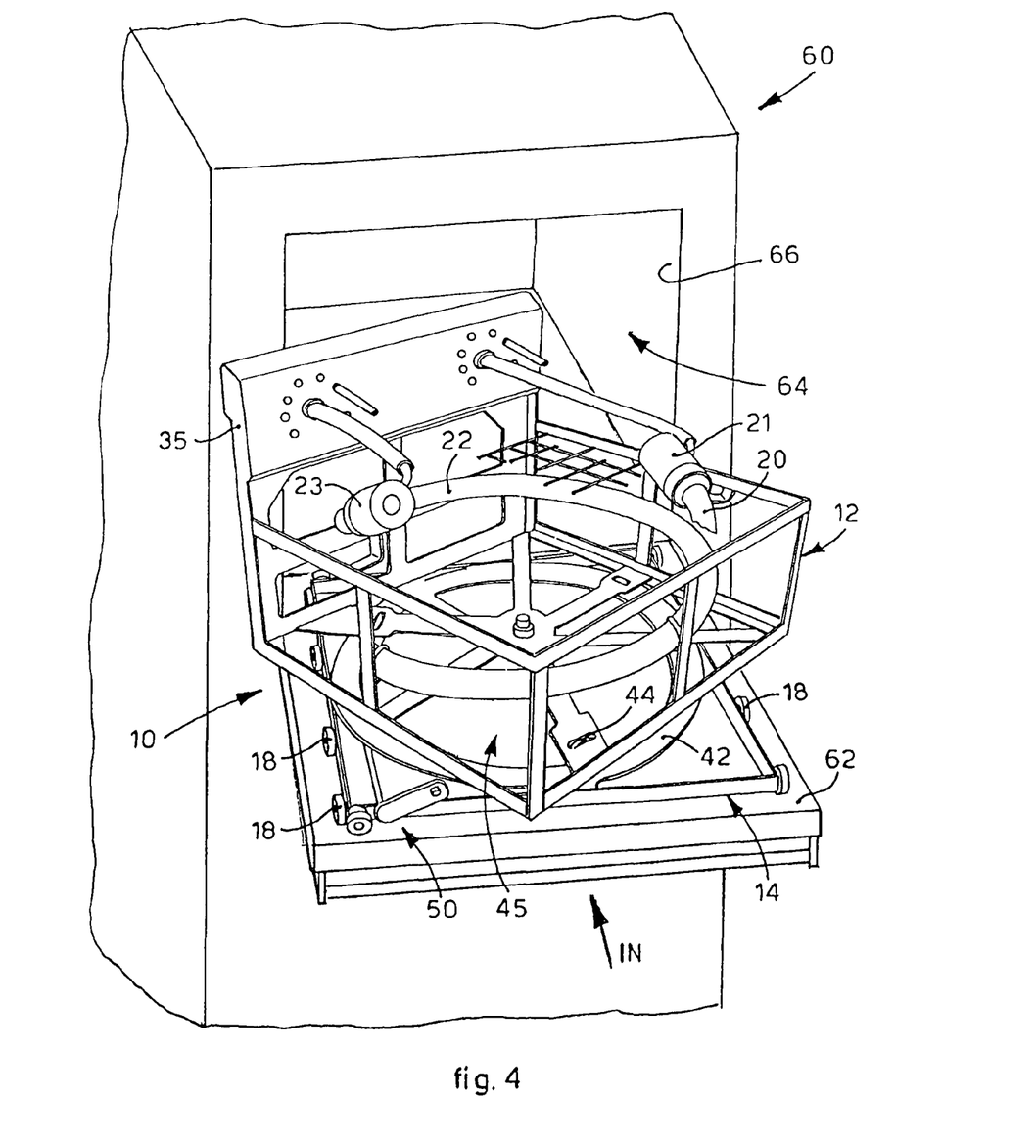
FIG. 4 is a perspective view of a container according to the present invention associated with a washing machine.

With reference to the attached drawings, a loading container 10 according to the present invention is used to position, support and load objects to be washed, or relative washing devices 20, 22 inside which the objects to be washed are inserted, inside a suitable washing machine 60 (FIG. 4). The washing machine 60 normally has an aperture 66 for insertion in a washing chamber 64, selectively closed by a flap door 62. The flap door 62, in its horizontal lowered position, acts as a sliding plane for the insertion of the container 10.

Typically, the objects to be washed, or the washing devices 20, 22, have a univocal geometric configuration in relation to the loading and washing operations in the washing machine 60, presenting their specific functional parts, which must be easily accessible for the operator, toward the operator. Moreover, the container 10 has a geometry mating with that of the aperture 66, so as to have a univocal insertion position into the washing chamber 64.

In this case the containing body 12 supports a first 20 and a second 22 spiral washing device, of a known type, for example from EP'868, inside which a relative inserted endoscope (not shown in the drawings) is washed, both internally and externally.

The container 10 comprises a containing body 12, a base body 14 and a rotation unit 45 for the relative rotation of the containing body 12 and the base body 14. The containing body 12 is disposed above and the base body 14 is located below the containing body 12.

The containing body 12 is able to support the objects to be washed or washing devices inside which the objects to be washed are inserted, while the base body 14 is used for the linear translation of everything.

Figure 3:
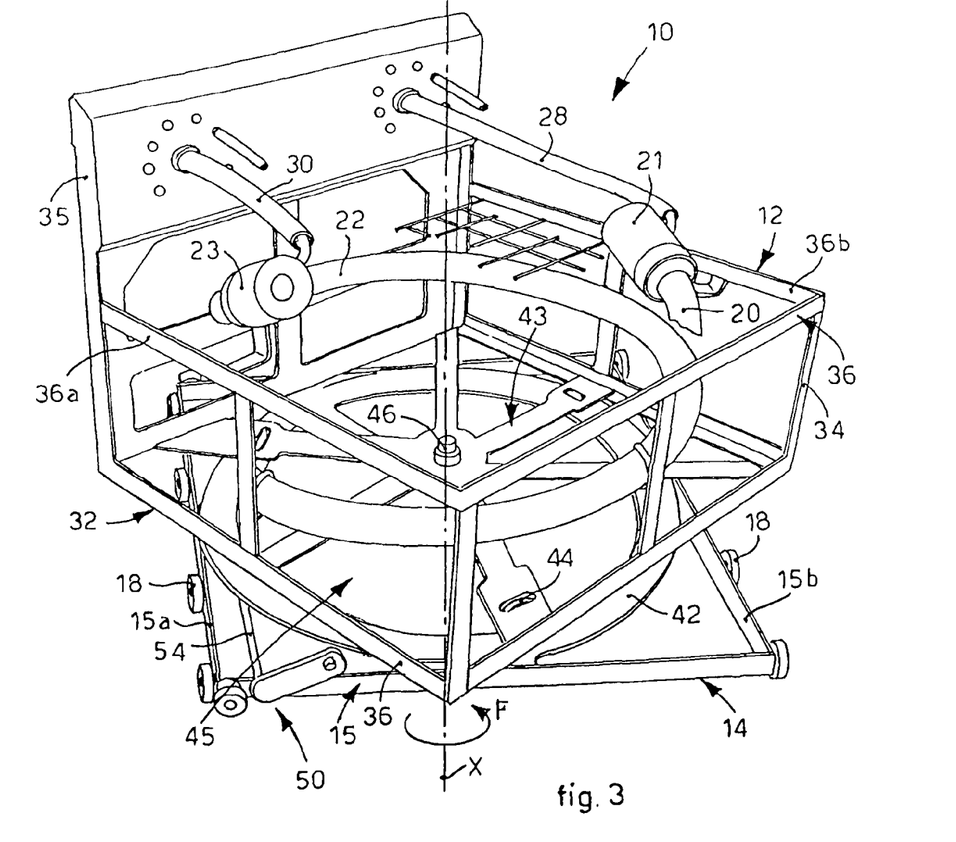
FIG. 3 is a perspective view of a container according to the present invention in a second condition of use.

The rotation unit 45 is interposed between the containing body 12 and the base body 14 and is able to connect rotatably the containing body 12 to the base body 14, so as to allow the relative rotation of the containing body 12 and the base body 14, around a common axis of rotation X, arrow F (FIG. 3). In particular, thanks to the rotation unit 45, the containing body 12 can selectively rotate on itself by at least about 180° with respect to the base body 14 which remains still, for example in an anti-clockwise direction as indicated by arrow F in FIG. 3. The extent of the rotation can be free, even 360° or more, or pre-set to determinate angular extents, although the possibility remains of clamping, by choice, the rotation by means of a clamping device 50, which will be described in detail hereafter in the description.

The base body 14 is formed by a horizontal base frame 15, of a rectangular or square shape, having, on two opposite sides 15a and 15b, a row of sliding rollers 18 to facilitate the insertion by sliding on the lowered flap door 62 of the container 10 inside the washing chamber 64, in the direction indicated by the arrow IN in FIG. 4. The sliding rollers 18 make the container 10 according to the invention of the trolleyed type and easily movable linearly without much effort.

The containing body 12 is formed, in this case, by a lower frame 32 and by an upper frame 36, horizontal and opposite each other, of a shape mating with that of the base frame 15.

The two frames lower 32 and upper 36 are connected with respect to each other by a plurality of peripheral vertical uprights 34. The upper frame 36 supports and positions a grid type plane 40, for easy draining of the washing liquid. Moreover, on opposite sides 36a, 36b, the upper frame 36 has brackets 16 which have support rings 17, into which sleeves 21 and 23 of the first washing device 20 and the second washing device 22 are inserted in order to be supported and clamped.

Figure 2:
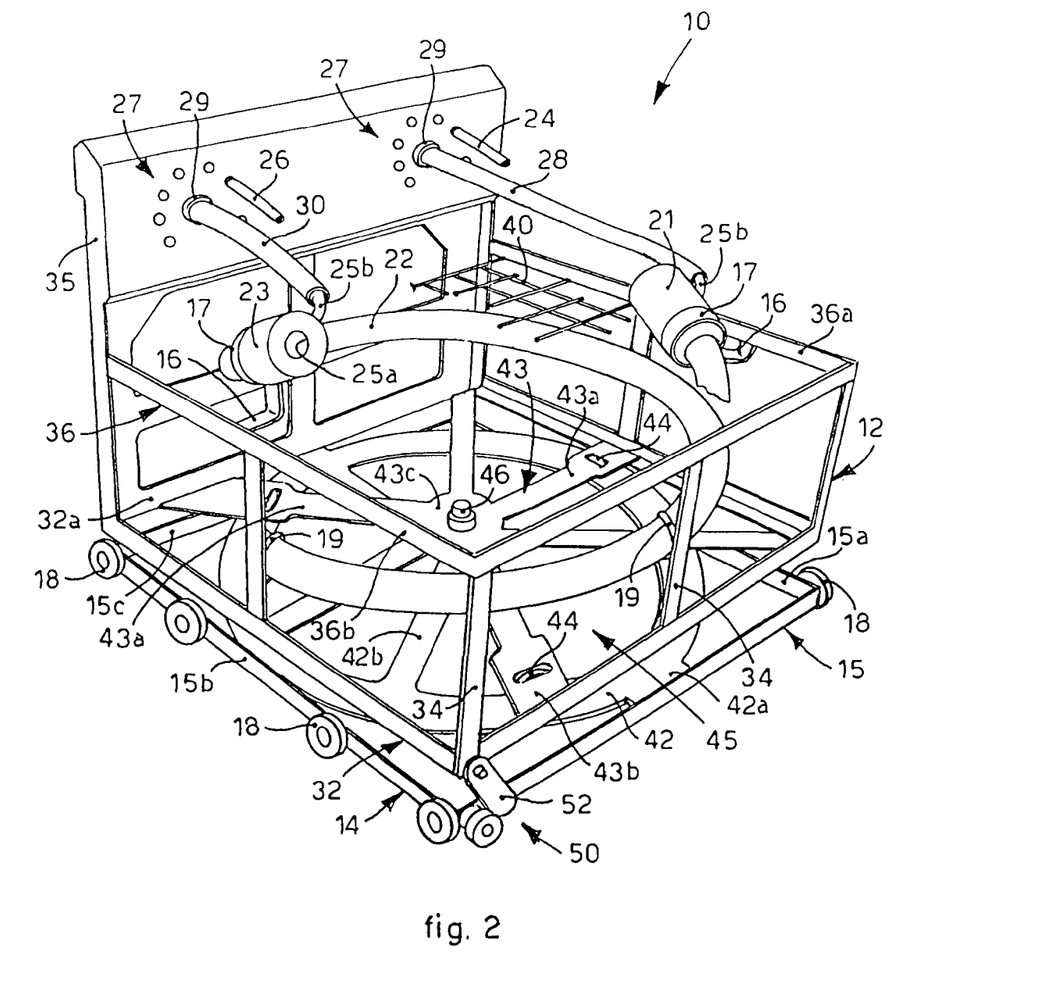
FIG. 2 is a perspective view of a container according to the present invention in a first condition of use.

In this way, the sleeves 21, 23 normally present themselves to the operator, as shown in FIG. 2, one facing forward and the other facing backward with respect to the direction of insertion into the washing machine 60. Each of said sleeves 21, 23 has both an axial entrance 25a, into which one or more tubes of a bundle of washing tubes 24, 26 can be inserted, to wash the inside of the endoscope and its internal channels, and also a transverse hydraulic connection 25b in order to connect a pipe 28, 30 to wash the outside of the endoscope.

The vertical uprights 34, in this case those in the central position with respect to each side of the two frames 32 and 36, are provided with a vertical row of auxiliary rings 19, toward the inside of the containing body 12, into which auxiliary rings 19 the spirals of the washing devices 20, 22 can be inserted.

On one side 32a of the lower frame 32, transverse to said sides 36a, 36b of the upper frame 36, a vertical wall 35 extends upward, and develops in height even above the level of the upper frame 36. The vertical wall 35, during the normal use of the container 10 in insertion condition, faces the opposite way with respect to the position of the operator, and therefore toward the inside of the washing chamber 64.

On the part of the vertical wall 35 which protrudes further than the upper frame 36 there are two units of hydraulic connectors 27 for the bundles of washing tubes 24, 26 (in FIGS. 2, 3 and 4 only one washing tube is shown for ease of illustration), which can be inserted axially into the sleeves 21, 23 for washing the internal pipes of the endoscope, and two hydraulic connectors 29 for the two pipes 28, 30 which are connected laterally to the corresponding sleeves 21, 23 for washing the outside of the endoscope. Moreover the hydraulic connectors 27, 29, are able to be connected to respective pumps and selective delivery circuits of the washing liquid, disinfectant and air for drying, not shown in the drawings.

Figure 3A:
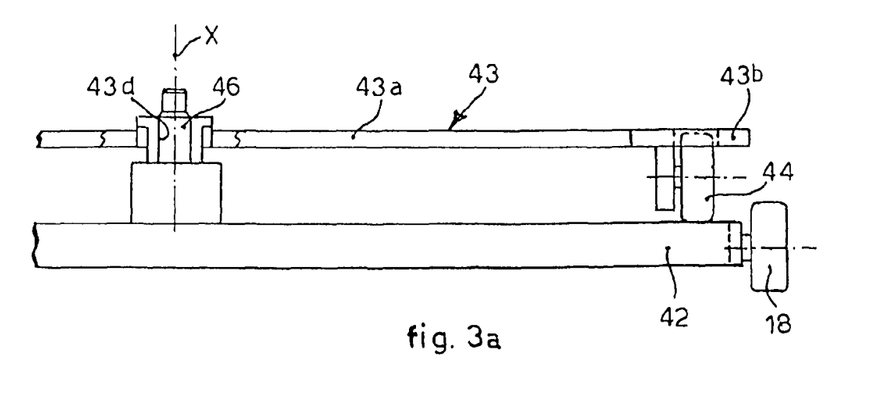
FIG. 3a is an enlarged detail of a part of the container according to the present invention.

According to one form of embodiment, the rotation unit 45 comprises, associated with the containing body 12, a support structure configured with a radial structure 43 provided with three wheels 44 and, associated with the base body 14, a rotation pin 46, to pivot the containing body 12 to the base body 14 and an annular sliding track 42 on which the wheels 44 slide when the containing body 12 rotates on itself (FIG. 3a).

The radial structure 43 is associated at the lower part with the lower frame 32. In this case, the radial structure 43 is formed by six radial plates or spokes 43a, angularly offset by 60°, the peripheral ends 43b of which are attached to the lower frame 32. In particular, three spokes 43a are provided, offset by 120°, on the peripheral ends 43b of which the sliding wheels 44 are rotatably assembled, vertical and with a radial axis of rotation with respect to the axis of rotation X. The other three remaining spokes 43a, offset by 120°, function to make the structure rigid and stable during rotation. Centrally, the radial structure 43 has a hub 43c with a rotation seating 43d, provided with a bearing or similar member in order to promote the rotation of the pin 46.

The annular track 42, on the other hand, is attached to the base frame 15, inside its bulk, by means of connection elements 42a; it is provided with spokes 42b and centrally supports and positions the rotation pin 46 facing upward, inserted in the rotation seating 43d of the radial structure 43.

The wheels 44 of the radial structure 43 rest slidingly directly on the annular track 42 below, and are able to roll along the circumference defined by the annular track 42.

The base body 14 is associated with the clamping device 50 described above, in order to selectively clamp the rotation of the containing body 12 and the base body 14 in the desired position, the operating condition of alignment shown in FIG. 2.

The clamping device 50, in this case, for each side 15c of the base frame 15 transverse to said sides 15a, 15b, has a rotatable stopping lever 52, able to protrude upward, or other similar stopping element.

The stopping levers 52 are connected to a command rod 54 which develops adjacent and parallel to one of the two sides 15a, 15b, in this case the left side 15a in FIG. 3. Each stopping lever 52 can be rotated between a first clamping position, upward (FIG. 2), so as to protrude by a length such as to prevent the rotation of the upper containing body 12, and a second operating condition, downward (FIG. 3), in which it does not interfere with the rotation.

When the containing body 12 and the base body 14 are aligned, in particular as can be seen in FIG. 2 in which the container 10 is in the position which allows it to be univocally inserted through the aperture 66, it is possible to clamp this position by rotating the lever 52 upward and to proceed with the insertion into the washing chamber 64.

In the operating insertion position of FIG. 2, the respective base frame 15 and lower frame 32 and upper frame 34 are aligned, in particular it can be seen that the sides 15a and 15b of the base frame 15 are aligned with the sides 36a and 36b of the upper frame 36. On the other hand, in the rotated condition, the clamping device 50 is released from the containing body 12 and the operator can rotate the latter according to operating needs.

As a result, having rested the container 10 on the flap door 62, the operator can easily rotate the containing body 12, so as to position one of the sleeves 21, 23 in the position which is most congenial, normally at the front as can be seen in FIG. 4, in order to make the hydraulic connections. Once this operation has been completed, the operator, in order to reach even the parts of the washing devices 20, 22 which are most distant, can rotate the containing body, for example by 180°, so that the other sleeve 21, 23 is automatically in a favorable position and close to the operator, so as to achieve the hydraulic connection with this one too.

At the end of the hydraulic connection operations, the containing body 12 is again aligned with the base body 14 by means of rotation on itself around the axis X, the clamping device 50 is activated and everything is positioned inside the washing chamber 64 to start the treatment and washing cycle.

In some forms of embodiment, each stopping lever 52 comprises, or is associated with, an automatic return mechanism from the second operating condition, facing downward, to the first clamping position, facing upward, of the stopping levers 52. This increases the safety in use of the present invention in that it guarantees, in substance, that the containing body 12 is always inserted into the washing chamber 64 by the user, clamped in the correct position of alignment with respect to the base body 14, so that the operator does not need to manually rotate the stopping levers 52. In some forms of embodiment, the automatic return mechanism can be of the elastic type and comprise elastic means, possibly pre-loaded, for example it can comprise a helicoidal spring, an axial spring or other equivalent mechanisms, associated with the command rod 54.

The invention claimed is:

1. A loading container for a washing machine (60), the loading container comprising:
    a containing body (12) able to support and position objects to be washed inside the washing machine (60) or washing devices (20, 22) containing said objects to be washed;
    a base body (14) located below the containing body (12); and
    a rotation unit (45) able to rotatably connect the base body (14) and the containing body (12) to allow a selective reciprocal angular positioning of the containing body (12) and the base body (14), said rotation unit (45) comprising:
        a supporting and sliding wall comprising an annular sliding track (42) attached to the base body (14) which comprises a rotation pin (46);
        a support structure (43) attached below the containing body (12), which has a rotation seating (43d) for said rotation pin (46), in order to pivot said containing body (12) to said rotation pin (46) to slide in rotation along said supporting and sliding wall; and
        second sliding means (44) suitable to cooperate with said annular sliding track (42), slidingly resting directly on the annular track (42) and being able to roll along the circumference defined by the annular sliding track (42).

2. The container according to claim 1, wherein the base body (14) is provided with first sliding means (18) to be translatable linearly.

3. The container according to claim 1, wherein the rotation unit (45) is conformed to allow relative rotation of the containing body (12) and the base body (14) around an axis of rotation (X) passing substantially through a center of said containing body (12) and said base body (14).

4. The container according to claim 1, wherein the supporting and sliding wall is attached inside the base body (14).

5. The container according to claim 1, wherein said second sliding means comprises wheels (44).

6. The container according to claim 1, wherein the support structure is configured in a radial arrangement (43) comprising a plurality of radial plates (43a) having peripheral ends (43b) that bear on the second sliding means (44).

7. The container according to claim 6, wherein said radial arrangement is a radial support structure (43) formed by six radial plates or spokes (43a) angularly offset by 60°, having peripheral ends (43b) attached to the containing body (12).

8. The container according to claim 1, wherein the annular track (42) is attached to said base body (14) by means of connection elements (42a) and is provided with spokes (42b) and centrally supports and positions, facing upwardly, said rotation pin (46).

9. The container according to claim 1, further comprising a clamping device (50) able to be selectively driven to allow clamping of a relative rotation of said containing body (12) and said base body (14).

10. The container according to claim 9, wherein said clamping device (50) comprises a rotatable stopping lever (52), able to protrude upwardly, and connected to a command rod (54), the rotatable stopping lever (52) being able to rotate between a first clamping position to protrude by a length such as to prevent rotation of the containing body (12) and a second operating condition in which the stopping lever does not interfere with the rotation.

11. The container according to claim 10, wherein the rotatable stopping lever (52) of the clamping device (50) comprises an automatic return mechanism from the second operating condition of non-interference with said containing body (12) to the first clamping condition of the containing body (12).

12. The container according to claim 1 wherein the base body (14) comprises a horizontal base frame (15) of a rectangular or square shape, the containing body (12) being formed by a lower frame (32) and by an upper frame (36), horizontal and opposite each other, of a shape mating with that of the base frame (15), said two frames (32, 36) being connected to each other by a plurality of peripheral vertical uprights (34), said upper frame (36) supporting and positioning a grid type plane (40).

13. The container according to claim 12, wherein the vertical uprights (34) are provided with a vertical row of auxiliary rings (19) toward an inside of the containing body (12).

14. The container according to claim 12, wherein, on opposite sides (36a, 36b), the upper frame (36) has brackets (16) which have support rings (17) into which sleeves (21, 23) of a first washing device (20) and of a second washing device (22) are able to be inserted in order to be supported and clamped, one of said sleeves (21, 23) normally facing forward and the other facing backward with respect to a direction of insertion into the washing machine (60), each of said sleeves (21, 23) having both an axial entrance (25a) into which one or more tubes of a bundle of washing tubes (24, 26) can be inserted and a transverse hydraulic connection (25b) in order to connect a washing pipe (28, 30).

15. The container according to claim 14, wherein, on one side (32*a*) of the lower frame (32), transverse to said opposite sides (36*a*, 36*b*) of the upper frame (36), a vertical wall (35) extends upwardly and develops in height even above a level of the upper frame (36), on the part of the vertical wall (35) which protrudes further than the upper frame (36) being two units of hydraulic connectors (27) for bundles of washing tubes (24, 26) and two hydraulic connectors (29) for two washing pipes (28, 30).

\* \* \* \* \*